(12) United States Patent
Bonazzoli et al.

(10) Patent No.: US 9,760,767 B1
(45) Date of Patent: Sep. 12, 2017

(54) RATING APPLICATIONS BASED ON EMOTIONAL STATES

(71) Applicant: International Business Machines Corporation, Armonk, NY (US)

(72) Inventors: Simone Bonazzoli, Rome (IT); Marco Borgianni, Rome (IT); Claudio Falcone, Rome (IT); Alessio Fioravanti, Rome (IT); Giuseppe Longobardi, Naples (IT); Silvano Lutri, Rome (IT); Luigi Presti, L'Aquila (IT); Paolo Salerno, Rome (IT); Alessandro Tomasi, Latina (IT); Francesca Ziantoni, Rome (IT)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/276,967

(22) Filed: Sep. 27, 2016

(51) Int. Cl.
G06K 9/00 (2006.01)
H04L 29/06 (2006.01)
(Continued)

(52) U.S. Cl.
CPC ........ *G06K 9/00315* (2013.01); *A61B 5/0077* (2013.01); *A61B 5/165* (2013.01);
(Continued)

(58) Field of Classification Search
None
See application file for complete search history.

(56) References Cited

U.S. PATENT DOCUMENTS

| 8,462,996 B2 | 6/2013 | Moon et al. |
| 2006/0143647 A1* | 6/2006 | Bill .................. G06F 17/30743 725/10 |

(Continued)

FOREIGN PATENT DOCUMENTS

WO 9804083 A2 1/1998

OTHER PUBLICATIONS

Microsoft Rate My App(extracted from https://github.com/Microsoft/rate-my-app/blob/master/README.md, updated Nov. 2014).*

(Continued)

*Primary Examiner* — Mark Roz
(74) *Attorney, Agent, or Firm* — Patterson + Sheridan, LLP (57) ABSTRACT

Method and apparatus for rating applications. Execution of an application on a computing device is monitored to determine usage information for a user. Embodiments capture a plurality of images and for each of the plurality of images, extract, from the respective image, a set of user facial features and determine an user emotional state corresponding to the respective set of user facial features by applying a model correlating a set of predefined emotional states with corresponding predefined facial features. A trend of user emotional states across a plurality of executions of the application on the computing device is determined. Embodiments calculate a rating for the application based on the usage information, the user emotional states, and the trend of the user emotional states. The rating is sent to a server over a network connection for use in an aggregate rating of the application.

20 Claims, 5 Drawing Sheets

(51) Int. Cl.
*G06F 17/30* (2006.01)
*G06K 9/62* (2006.01)
*A61B 5/00* (2006.01)
*A61B 5/16* (2006.01)

(52) U.S. Cl.
CPC ..... *G06F 17/3028* (2013.01); *G06K 9/00255* (2013.01); *G06K 9/00268* (2013.01); *G06K 9/6212* (2013.01); *H04L 67/42* (2013.01); *A61B 2503/12* (2013.01)

(56) References Cited

U.S. PATENT DOCUMENTS

| | | | |
|---|---|---|---|
| 2010/0030714 A1* | 2/2010 | Bollano | G10L 17/26 706/12 |
| 2013/0086519 A1* | 4/2013 | Fino | G06Q 30/02 715/810 |
| 2013/0232256 A1 | 9/2013 | Lee et al. | |
| 2014/0006418 A1 | 1/2014 | Forte et al. | |
| 2014/0316881 A1 | 10/2014 | Movellan et al. | |
| 2015/0039405 A1 | 2/2015 | Frank et al. | |

OTHER PUBLICATIONS

Wooldridge ("The Business of iPhone and iPad App Development", Springer, copyright 2011).*

Nader ("Climbing App Store Charts with App Ratings and Reviews", retrieved from http://blog.apps-builder.com/app-ratings-and-reviews/, available as of Feb. 2015).*

* cited by examiner

| FIRST SAMPLE SET OF SCORES 510 (RELATIVELY DISGUSTED) | |
|---|---|
| HAPPINESS | 20 |
| SADNESS | 00 |
| SURPRISE | 00 |
| ANGER | 10 |
| FEAR | 00 |
| DISGUST | 40 |
| NEUTRAL | 30 |
| FATIGUE | 00 |
| EMOT STATE = -30 | |

| SECOND SAMPLE SET OF SCORES 520 (RELATIVELY NEUTRAL) | |
|---|---|
| HAPPINESS | 10 |
| SADNESS | 00 |
| SURPRISE | 00 |
| ANGER | 00 |
| FEAR | 00 |
| DISGUST | 00 |
| NEUTRAL | 85 |
| FATIGUE | 05 |
| EMOT STATE = 5 | |

| THIRD SAMPLE SET OF SCORES 530 (RELATIVELY DISGUSTED) | |
|---|---|
| HAPPINESS | 60 |
| SADNESS | 10 |
| SURPRISE | 00 |
| ANGER | 00 |
| FEAR | 00 |
| DISGUST | 00 |
| NEUTRAL | 30 |
| FATIGUE | 00 |
| EMOT STATE = 50 | |

RATING APPLICATIONS BASED ON EMOTIONAL STATES

BACKGROUND

The present disclosure relates to rating applications, and more specifically, to calculating a rating for an application based on a determined emotional state of a user and on usage information regarding the application.

Conventional methods for rating applications can be inaccurate for many reasons. Typically users must actively make a decision to submit a rating, and therefore many users do not submit a rating. Additionally, all user-submitted ratings are typically weighted equally to create an aggregate rating for the application, regardless of the user's usage of the application. For example, a rating from one user that only used the application once is conventionally weighted equally to a rating from another user that extensively used the application.

SUMMARY

According to one embodiment described herein, a method for determining a rating includes: monitoring execution of an application on a device to determine usage information for a user; capturing (e.g., via a user-facing camera of a mobile device) a plurality of images of the user's face; for each of the plurality of images (using one or more computer processors of the computing device) extracting (from the respective image) a set of user facial features, and determining a user emotional state corresponding to the respective set of user facial features by applying a model correlating a set of predefined emotional states with corresponding predefined facial features; determining a trend of the user emotional states across a plurality of executions of the application on the device; calculating a rating for the application based on the usage information, the user emotional states, and the determined trend of the emotional states; and sending the rating to a remote server for use in determining an aggregate rating of the application.

BRIEF DESCRIPTION OF THE SEVERAL VIEWS OF THE DRAWINGS

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Conventional techniques for determining an average rating for an application across a plurality of users suffer from several deficiencies. For example, most users do not bother to input ratings at all. As a result, the potential feedback that could be collected from these users cannot be considered in the aggregate rating for the application. As another example, a rating from an "amateur" user (e.g., a user who has only used the application twice) is typically treated equally in value with a rating from a "professional" user (e.g., a user who has used the application 50 times). As such, although the "professional" user may be in a better position to provide a review of the application, no additional weight is conventionally allocated to the "professional" user's review.

Embodiments described herein generally determine a rating for an application, based on a determined emotional state of a user interacting with the application and usage information (such as the number of times the application has been used). For example, a rating determination component could monitor executions of an application on a computing device to determine usage information for a user. Such usage information could include, for example, a frequency of usage of the application (also referred to herein as a utilization rate), a duration of usage of the application, and so on. The rating determination component could capture, using a user-facing camera of the computing device, a plurality of images of the user's face. The rating determination component could then analyze each of the plurality of images by extracting, from the respective image, a set of user facial features and determining a user emotional state corresponding to the respective set of user facial features by applying a model correlating a set of predefined emotional states with corresponding predefined facial features. The rating determination component could calculate a rating for the application based on the usage information and the determined user emotional states. The rating determination component could then send the rating to a remote server for use in determining an aggregate rating of the application.

According to one embodiment, a rating determination component creates customized user profiles for each user of a computing device (e.g., a mobile device), determines which user is using the computing device (e.g., through face recognition, a PIN, a fingerprint, or other authentication method), and then applies the current user's customized user profile to determine the current user's emotional state. Additionally, in a particular embodiment, the rating determination component is configured to consider a trend of the determined user emotional states across a plurality of executions of the application. For example, the rating determination component could determine, based on the user emotional states determined based on the images of the user, that the user's mood tends to improve over time as the user uses the application. In response, the rating determination component could then determine a more favorable rating for the application for the particular user (e.g., relative to a circumstance where the user's mood tends to decline or stay the same while using the application).

Figure 1:
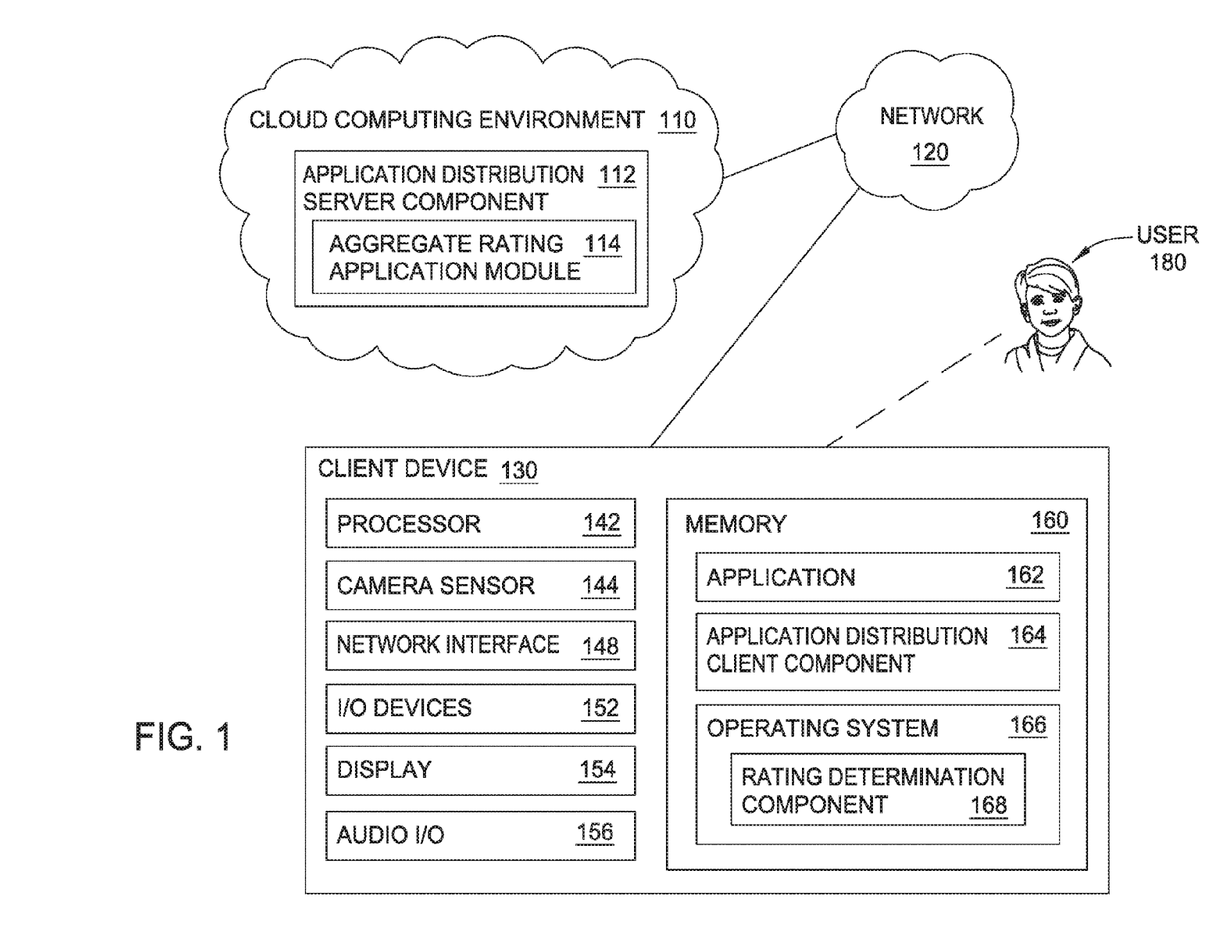
FIG. 1 illustrates a block diagram of a rating system including a cloud computing environment, a network, and a client device including an application and a rating determination component, according to one embodiment described herein.

FIG. 1 illustrates a block diagram of a rating system including a cloud computing environment 110, a network 120, and a client device 130. User 180 represents the current user of the client device 130 and may be one of several users of the client device 130. Each user may have their own PIN (Personal Identification Number) for accessing the client device 130. The cloud computing environment 110 may include an application distribution server component 112 having an aggregate rating application module 114. The network 120 provides communication between the cloud computing environment 110 and the client device 130.

The client device 130 may include a memory 160 storing an application 162, an application distribution client component 164, and an operating system 166 having a rating determination component 168. The client device 130 may include hardware components such as a processor 142, a camera sensor 144, an network interface 148 for communication wirelessly with the network 120, I/P devices 152, a display 154, and audio I/O (input/output) 156 such as a microphone and a speaker. The camera 144 may be a user facing camera configured to capture images of the current user during usage of the application.

Generally, the application distribution server component 112 provides an API through which users can retrieve information about applications and, if authorized, can download a copy of the applications. In doing so, the application distribution server component 112 could be configured to authenticate the user and to process payment information for the user. For instance, the application distribution server component 112 may authenticate the identity of the user using username and password information received from the client device 130 and could determine whether the authenticated user is authorized to download an application. As an example, the application distribution server component 112 could be configured to process payment information and could determine that the user is authorized to download the application only upon successfully processing the payment information. In the depicted example, application 162 has been downloaded from the application distribution server component 112, upon the application distribution server component 112 authenticating a particular user of the client device 130 and determining that the particular user is authorized to download the application 162. Additionally, the application distribution server component 112 can collect rating information for each application from users and could use such rating information to determine an aggregate rating for each application. This aggregate information can be provided to users through the provided API.

Generally, the rating determination component 168 is configured to determine a rating of an application based upon user emotional state information and application usage information. In doing so, the rating determination component 168, upon determining that the application 162 is executing on the client device 130, could capture images using camera 144. Camera 144 may be a user-facing camera of a smart phone, a tablet, a portable computer, or, for example, may be an externally mounted webcam of a desktop computer. Multiple cameras may be used. For example, a separate, mounted, very high quality external camera may be used to generate a user profile whereas the user-facing camera of the smart phone may be used to capture images for determining emotional states. Camera 144 may capture a fixed number of images during each execution of the application 162 or may capture images periodically (e.g., at one minute intervals) during each execution of the application 162. The rating determination component 168 can analyze the captured images to extract a user's facial features and can determine the user's emotional state based on the extracted facial features. Additionally, the rating determination component 168 can be configured to determine a trend for the user's emotional state across a plurality of images, e.g., across a plurality of executions of the application 162.

Additionally, the rating determination component 168 can collect usage information describing a particular user's usage of the application 162. For example, such usage information could specify how many times a particular user executed the application 162, an average duration for which the user executed the application 162, a frequency at which the user executes the application 162, and so on. More generally, the usage information could be any information describing a particular user's usage of the application 162. In the depicted embodiment, the rating determination component 168 is implemented as a component of the operating system 166 of the client device 130. Doing so helps to ensure that the rating determination component 168 will have sufficient permissions/access to monitor the usage of various applications on the client device 130, for use in automatically rating the applications.

The rating determination component 168 could then use the emotional state information and the usage information to calculate a rating for the application 162, for the particular user. For example, the rating determination component 168 could be configured to determine a first rating based on the determined user emotional state information and to determine a second rating based on the usage information. The rating determination component 168 could determine a final rating for the application for the user, based on the first rating and the second rating. For example, the rating determination component 168 could determine the final rating by calculating a weighted average of the first rating and the second rating. The rating determination component 168 could then transmit the final rating to the application distribution server component 112, e.g., for use in calculating an aggregate rating for the application across multiple users.

Figure 2:
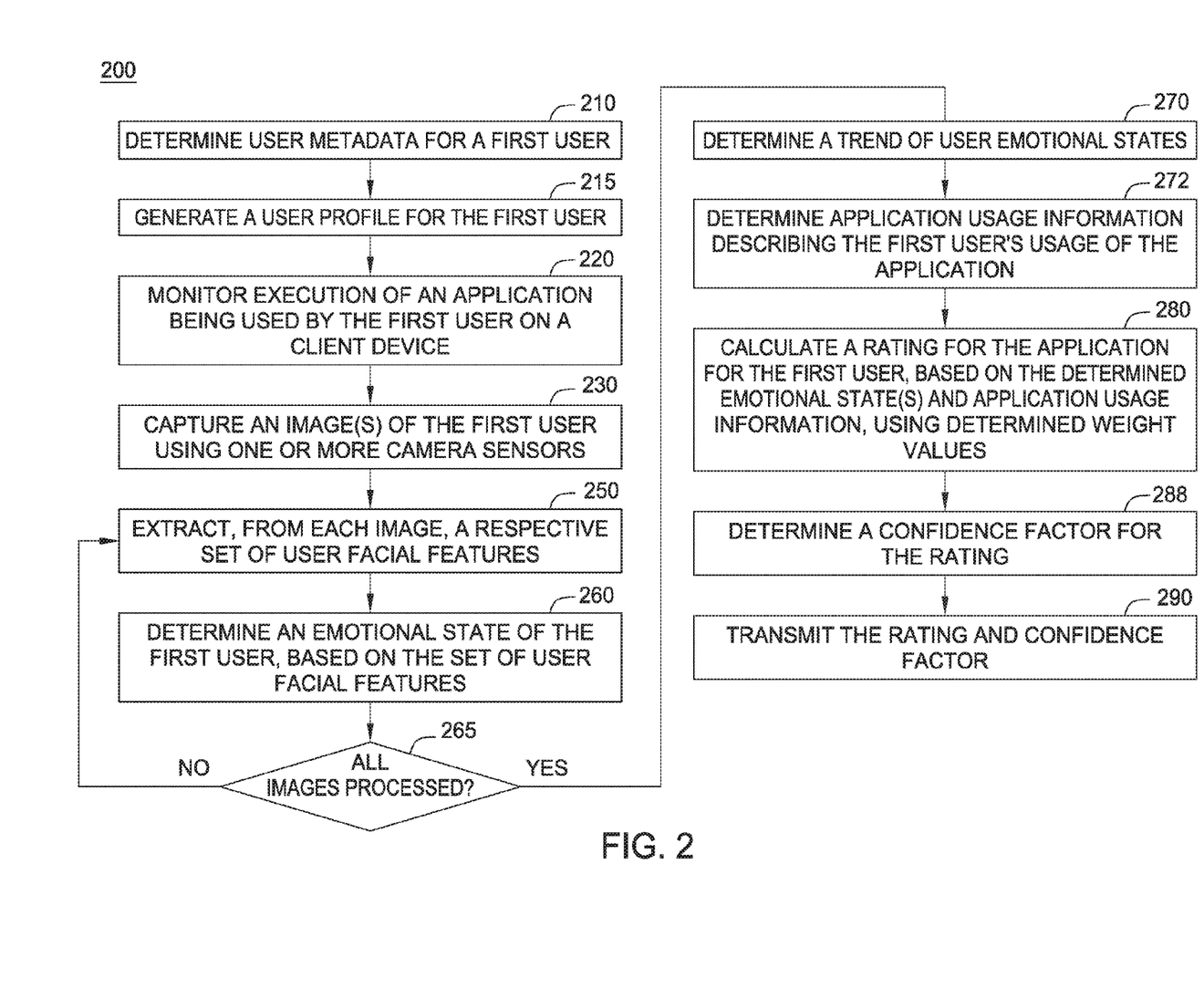
FIG. 2 is a flowchart illustrating a method of determining a rating based on determined user emotional states and usage information of the application according to one embodiment described herein.

FIG. 2 is a flowchart illustrating a method of determining a rating based on determined user emotional states and usage information of the application according to one embodiment described herein. The method 200 begins at block 210, the rating determination component 168 determines user metadata for one or more users of client device 130. Generally, the user metadata can contain any information describing an attribute(s) of the user. For instance, the user metadata could specify the user's age, gender, geographic location and so on. For example, the rating determination component 168 could be configured to retrieve the user metadata from the user's social networking page or other sources of information.

At block 215, the rating determination component 168 generates a user profile for the user. Such a user profile could specify a customized user model correlating facial features of the user with multiple predefined emotional states. In doing so, the rating determination component 168 can consider historical facial feature information for the particular user. For example, the rating determination component 168 could consider historical facial feature information for the particular user, e.g., facial feature data indicative of how the particular user smiles, facial feature data indicative of how the particular user frowns, etc. In one embodiment, the rating determination component 168 is configured to perform a calibration operation in order to determine the historical facial feature information for the particular user. For instance, the rating determination component 168 could request, using a user interface, that the user smile, and the rating determination component 168 could then capture an image of the user. The rating determination component 168 could extract a set of facial features from the captured image and could save the set of facial features in the user profile for the user, for use in identifying when the user is smiling in subsequent images.

At block 220, the rating determination component 168 monitors execution of application 162 and stores usage data. For example, such usage data could include a number of times that the user executed the application. As another example, the usage data could specify a number of minutes that the user executed the application. More generally, the rating determination component 168 can store any data that describes the usage of the application on one or more client devices.

At block 230, the rating determination component 168 captures images of the current user (e.g., using camera 144). For example, the rating determination component 168 could capture an image of the user at regular intervals (e.g., every minute) during execution of the application 162. In one embodiment, the rating determination component 168 is configured to wait a predetermined period of time after the user has initiated executed of the application, before beginning to capture the images. The rating determination component 168 can additionally record metadata describing each captured image, with such metadata including, for example, an identity of the user, a time of capture, an identity of the application being executed, and so on. The rating determination component 168 could then process the images to determine a user emotional state for the user of the application. In the depicted embodiment, the rating determination component 168 processes the images using batch processing. In a particular embodiment, the rating determination component 168 is configured to process each image after the image is captured.

At block 250, the rating determination component 168 extracts user facial features from a captured image of the current user. The rating determination component 168 may identify points (or nodes) in the pixels of the captured image that correspond to points on physical features of the user's face such as corners of the mouth, corners of the eyes, corners of the eyebrows, bottom of the chin, outside corners of nostrils, highest point and lowest point of eyes, etc. These physical features may be analyzed to determine facial features that may be associated with emotions. For example, upward curvature of the ends of the mouth may indicate a smile facial feature. Other facial features may include placement of the eyelids. Closed eyes (or almost closed eyes) may indicate a fatigue facial feature. Further, such physical features may be used to identify or authenticate the user.

At block 260, the rating determination component 168 determines an emotional state based upon the captured image and the user profile. For example, a model may correlate a smile facial feature (a mouth with upward curvature at the corners) to a happy emotional state. In general, the model may correlate a set of predefined emotional states with corresponding predefined facial features. In a particular embodiment, the rating determination component 168 can use the information within the user profile for the user in determining the emotional state of the user. The captured image may then be deleted to preserve the user's privacy and to save memory.

At decision diamond 265, the rating determination component 168 determines whether all relevant images have been processed. Block 260 will loop back to blocks 250 and 260 to continue extracting user facial features and to determine user emotional states until all of the relevant images (captured at block 230) have been processed.

At block 270, the rating determination component 168 determines a trend for user emotional states across a plurality of executions of the application. That is, the rating determination component 168 could determine a user emotional state when the user first begins using the application and could then determine one or more subsequent user emotional states while the user is using the application, e.g., to determine whether the user's mood is improving (i.e., the user is becoming happier), getting worse or staying the same. For example, for a neutral emotional state followed by a happy emotional state indicates a trend of increasing happiness. The rating determination component 168 could consider such a trend in calculating a final rating for the application for the user. For instance, if the user's mood tends to improve each time the user uses a particular application, the rating determination component 168 could determine a relatively positive rating for the application for the user.

At block 272, the rating determination component 168 determines usage information for use in calculating a final rating for the application for the user. As discussed above, the usage information may include, without limitation, the number of times the application was executed, the accumulated execution time of the application, the frequency of execution of the application, and information regarding other applications stored on the client device or executed by the user.

At block 280, the rating determination component 168 calculates a final rating for the application for the user, based on the determined emotional states and the usage information, using determined weight values. For example, the rating determination component 168 could determine a first rating based on the determined emotional states and could determine a second rating based on the usage information. The rating determination component 168 could calculate a weighted average of the first and second ratings, using determined weight values. In one embodiment, the rating determination component 168 is configured to use predefined weight values to calculate the rating.

In a particular embodiment, the rating determination component 168 is configured to dynamically determine the weight values to use. For example, the rating determination component 168 could be configured with a plurality of demographic profiles, with each demographic profile specifying a respective set of weights to use in determining ratings. That is, different demographics of users (e.g., users in the age range of 10-15 years old, users in the age range of 30-40 years old, etc.) may generally tend to show more or less emotion in their facial expressions and may generally tend to have different application usage patterns. For example, for one demographic, the application usage information may be more indicative of how much the users in the demographic tend to like an application, whereas for another demographic, the user emotional states determined by analyzing images of the users of the demographic may be more indicative of how much the users in the demographic feel about the application. As such, the rating determination component 168 can associate each demographic profile with a respective set of weights that most accurately reflect the user's impression of the application.

At block 288, the rating determination component 168 calculates a confidence factor. For example, if the current user has executed application 162 many times, then the confidence factor may indicate a high confidence that the current user is providing an accurate rating. The application distribution server component could then consider such a confidence factor, for example, in calculating an aggregate rating for an application based on ratings from multiple different users. In one embodiment, the confidence factor may be a binary value that is set to "1" when the user has executed the application more than a predefined threshold number of times, and the confidence factor is set to "0" otherwise. More generally, many types of information may be considered for calculating the confidence factor. For example, in calculating the confidence factor, the rating determination component 168 may consider the number of times the application was executed, the accumulated execution time of the application, the frequency of execution of the application, and information regarding other applications stored on the client device or executed by the user.

At block 290, the rating determination component 168 transmits the rating and the confidence factor to the aggregate rating application module 114 via network 120. The aggregate rating application module 114 may then use the determined rating and the associated confidence factor (in combination with other determined ratings and associated confidence factors) to determine an aggregated rating for the application. This aggregated rating would avoid many of the problems of conventional ratings (such as equal value being given to each rating, despite unequal usage by the users).

Figure 3:
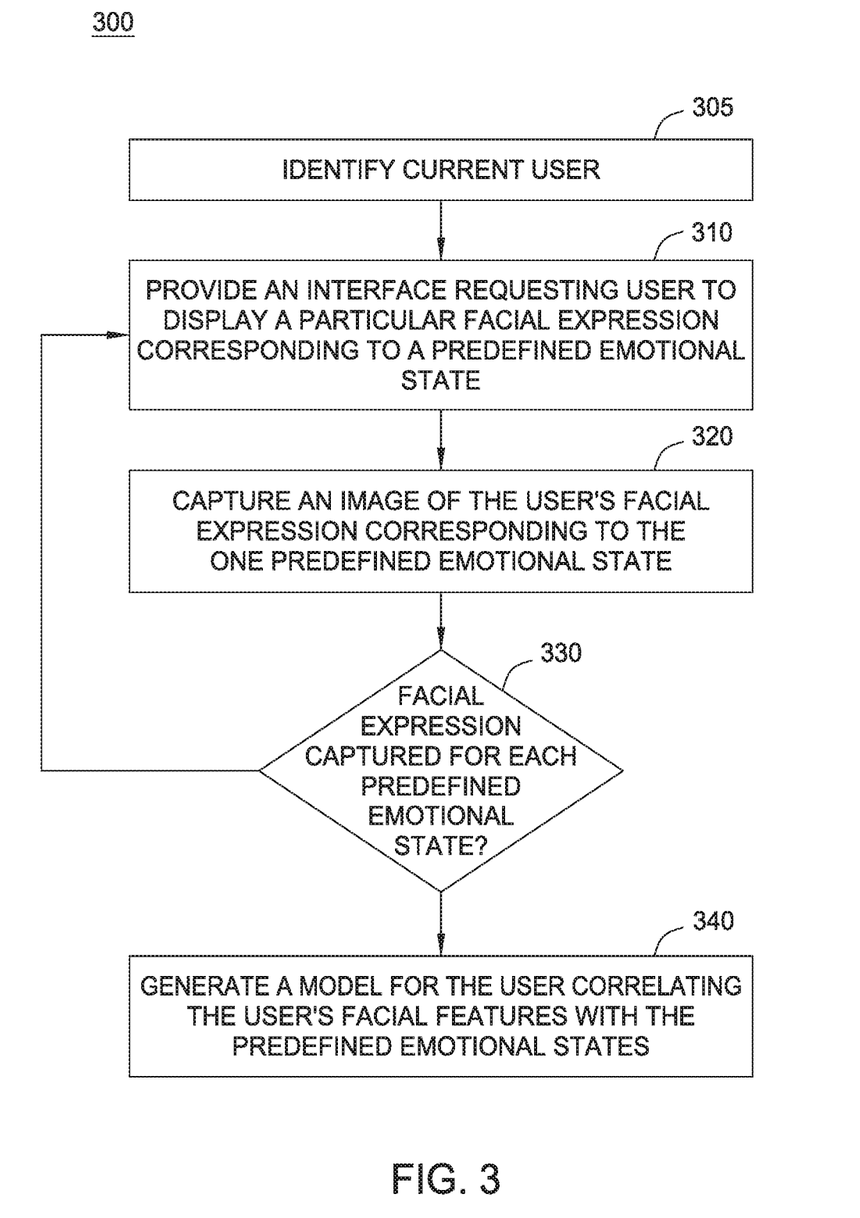
FIG. 3 is a flowchart illustrating a method of generating an individual user profile for every user of a computing device according to one embodiment described herein.

In one embodiment, the rating determination component 168 is configured to perform a calibration operation in order to learn how a particular user expresses various emotions. In doing so, the rating determination component 168 can effectively learn how a particular user's facial expressions reflect the user's emotional state, which in turn can enable the rating determination component 168 to more accurately determine emotional states from subsequent images of the user. An example of such an operation is shown in FIG. 3, which depicts a flowchart 300 illustrating a method of generating an individual user profile for every user of a computing device according to one embodiment described herein. FIG. 3 requests a current user to intentionally display one facial expression corresponding to one predefined emotional state, and then repeats the request for another predefined emotional state until a complete set of intentionally displayed facial expressions is captured corresponding to a complete set of predefined emotional states. This complete set of intentionally displayed facial expressions is then used to generate a user profile for the current user.

At block 305, the rating determination component 168 identifies a current user via a fingerprint, a PIN, facial recognition, or other authentication procedure. More generally, the rating determination component 168 can be configured to use any technique for authenticating a user, consistent with the functionality described herein. At block 310, the rating determination component 168 requests the current user to intentionally display one facial expression (such as a smile) that corresponds to one predefined emotional state (such as happiness). For example, the client device 130 may request the current user to display a smile by outputting, on the display, a graphical user interface requesting that the user smile.

At block 320, the rating determination component 168 captures an image using camera 144 upon a determination that a smile is being intentionally displayed by the user. Such a determination may be based upon the user pressing a camera button, or may be based upon recognizing an upward movement of the corners of the user's mouth.

At decision diamond 330, the rating determination component 168 determines whether a complete set of facial expressions has been captured for the user, corresponding to a set of predefined emotional states. The set of predefined emotional states may include: happiness, sadness, surprise, anger, fear, and disgust. Additional emotional states such as neutral and fatigue may be included. The set of predetermined emotional states is hereby defined as including at least two emotional states.

At decision diamond 330, if the complete set of facial expressions for the current user has not been captured, then blocks 310 and 320 are repeated for the next predefined emotional state (such as sadness). If the complete set of facial expressions for the current user has been captured, then a user profile is generated corresponding to the current user.

At block 340, the rating determination component 168 generates a user profile for the current user. The user profile may include a customized user model correlating facial features with each predefined emotional state. Doing so enables the rating determination component 168 to more accurately determine the emotional state of the particular user.

Figure 4:
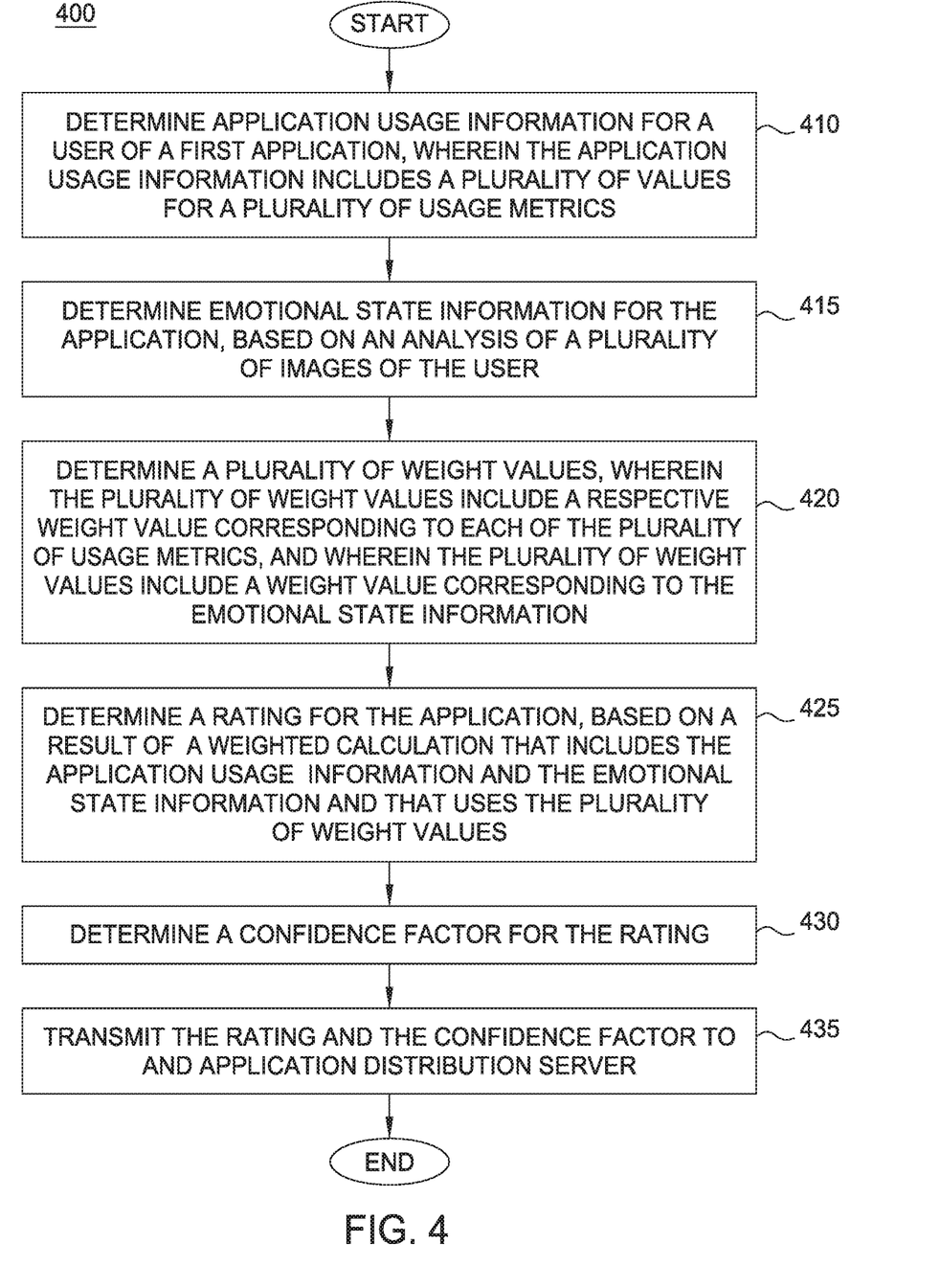
FIG. 4 is a flowchart illustrating a method of determining a rating for an application based on a result of a weighted calculation that includes application usage information, emotional state information, and a plurality of weight values according to one embodiment described herein.

FIG. 4 is a flowchart 400 illustrating a method of determining a rating for an application based on a result of a weighted calculation that includes application usage information, emotional state information, and a plurality of weight values according to one embodiment described herein.

In block 410, the rating determination component 168 determines application usage information for a user of an application, wherein the application usage information includes a plurality of values for a plurality of usage metrics. For example, the application was executed 15 times (a value of 15 for the usage metric of executions) and was executed for a total of 35 minutes (a value of 35 for a usage metric of total execution time).

In block 415, the rating determination component 168 determines emotional state information (for the user using the application) based on an analysis of a plurality of images of the user utilizing the user profile (including a customized user model correlating facial features with each predefined emotional state).

In block 420, the rating determination component 168 determines a plurality of weight values including a respective weight value corresponding to each of the plurality of usage metrics and including a weight value corresponding to the emotional state information. Exemplary usage metrics may include: a number of times the application has been executed by a particular user; a number of times the application has been executed on the particular client device; a frequency of execution of the application (e.g., by a particular user, on a particular device, etc.); a duration of execution (e.g., when executed by a particular user, when executed on a particular device, etc.); a total duration that the application has been executed (e.g., by a particular user, on a particular device, etc.) divided by a duration that all applications have been executed; etc.

For example, the weight value corresponding to the emotional state information may be relatively lower for a user that shows little emotion (a "low smiler"), and/or one or more of the weight values corresponding to the usage metrics may be increased for the user that shows little emotion.

In block 425, the rating determination component 168 determines a rating for the application, based on a result of a weighted calculation that includes the application usage information and the emotional state information and that uses the plurality of weight valued. For example: RATING=W1*(emotional state information)+W2*(first usage metric)+W3*(second usage metric) . . . . In this example, W1 is a weight value for emotional state information, W2 is a weight value for the first usage metric, and W3 is weight value for the third usage metric. For example, for a "low smiler," W1=0.2, W2=0.4, and W3=0.4. In contrast, for a "big smiler," W1=0.4, W2=0.3, and W3=0.3. More generally, any algorithm for calculating the rating can be used, consistent with the functionality described herein.

In block 430, the rating determination component 168 determines a confidence factor for the rating. In one embodiment, a confidence factor may be high when the application has been executed more than a predefined threshold number of times, and low otherwise. In another embodiment, a normalized confidence factor may range from 0.01 to 1.0 by the following equation: confidence factor=(number of executions)/100, wherein the number of executions is at least 1, but is limited to a maximum of 100. A confidence factor may also be generated by a look-up table. For example, the look-up confidence factor is 1 for 1 to 9 executions, the look-up confidence factor is 2 for 10 to 100 executions, and the look-up confidence factor is 3 for over 100 executions according to an exemplary look-up table.

In block 435, the rating determination component 168 transmits the rating and the confidence factor to an application distribution server. Further, blocks 410 through 435 may be repeated automatically over a predetermined period of time or over a predetermined number of executions of the application.

Figure 5:
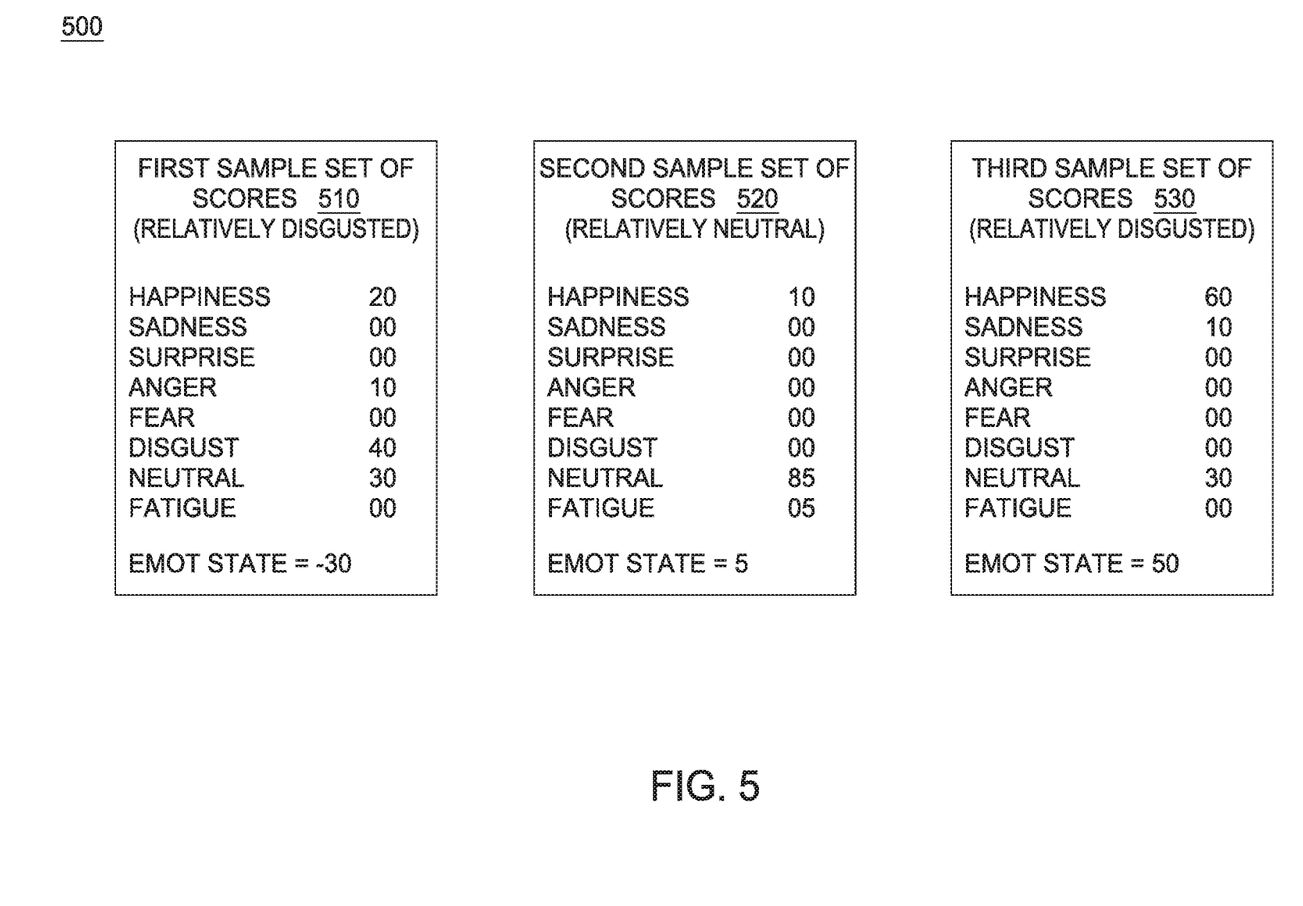
FIG. 5 is a block diagram of sample sets of scores illustrating a trend of improving emotional states over time according to one embodiment described herein.

FIG. 5 is a block diagram 500 of sample sets of scores (510, 520, and 530) illustrating a trend of improving emotional states over time according to one embodiment described herein. For example, scores 510 correspond to an emotional state of a user starting to execute an application, and indicate a relatively disgusted emotional state (emotional state=−30). Scores 520 correspond to an emotional state of the user at a midpoint of executing the application, and indicate a relatively neutral state (emotional state=5). Scores 530 correspond to an emotional state of the user upon termination of executing the application, and indicate a relatively happy state (emotional state=50).

The emotional state may be represented by a 1×8 matrix with 8 values (one value for each predetermined emotional state). Thus, the emotional state of the first sample set of scores 510 may be (20, 0, 0, 10, 0, 40, 30, 0). As another example, the emotional state may be represented by a single value, such as a single value of 30 for scores 510. More generally, any suitable format for specifying an indication of a user's emotional state can be used, consistent with the functionality described herein.

The emotional states illustrate (from left to right) a trend of improving emotional states (based upon the single value representations) of −30, 5, and 50 for scores 510, 520, and 530 respectively. As described above, a trend of improving emotional state may be used to improve a determined rating.

In one embodiment, the emotional states may be averaged to calculate a single average emotional state (for example, during one execution of the application). The average emotional state for FIG. 5 is: (−30+5+50)/3=8.3. Further, a weighted average emotional state may be calculated by weighting more recent emotional states more heavily than earlier emotional states. Such a weighted average emotional state is one way of incorporating trend information, such that an improving emotional state yields a better rating than a deteriorating emotional state. For example, a weighted average emotional state for FIG. 3 is: ((0.8)*(−30)+(1.0)*5+(1.2)*50)/3=13.6. The rating determination component 168 could then normalize the weighted average value to a rating metric used by the application distribution server component (e.g., a measure between 1 and 5 stars, a score out of 100, etc.). More generally, any metric for rating applications can be used, consistent with the functionality described herein.

The rating determination component 168 could then combine the normalized rating metric calculated from the average emotional state with a normalized metric calculated based on the user's usage of the application (e.g., using a second weighted average calculation). The rating determination component 168 could then transmit the resulting rating for the application to the application distribution server component, e.g., for use in generating an aggregate rating for the application across multiple users. Doing so enables a rating for the user to be automatically generated without user intervention, based on the user's usage of the application.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A computer-implemented method to rate applications based on weighted emotional states, the computer-implemented method comprising:
    monitoring execution of an application on a computing device to determine usage information for a user;
    capturing, via a user-facing camera of the computing device, a plurality of images;
    for each of the plurality of images, using one or more computer processors of the computing device:
        extracting, from the respective image, a set of user facial features; and
        determining an user emotional state corresponding to the respective set of user facial features by applying a facial-emotional model correlating a set of predefined emotional states with corresponding predefined facial features;

determining a trend of user emotional states across a plurality of executions of the application on the computing device;

calculating a rating for the application based on: (i) the usage information; (ii) the trend of user emotional states; and (iii) the user emotional states weighted by at least one of: (A) a demographic factor comprising a specified age group to which the user belongs and (B) an expressiveness factor comprising a variance of emotional expression of the user; and sending, via a network connection, the rating to a server configured to determine an aggregate rating of the application.

2. The computer-implemented method of claim 1, wherein each of the user emotional states is represented by a respective numeric value, and wherein calculating the rating for the application further comprises calculating an average of the respective numeric values.

3. The computer-implemented method of claim 1, wherein capturing the plurality of images is performed over a predefined period of time.

4. The computer-implemented method of claim 1, wherein capturing the plurality of images is performed over a predefined number of executions of the application.

5. The computer-implemented method of claim 1, wherein the sending the rating to the remote server occurs automatically a predefined period of time after the application is downloaded.

6. The computer-implemented method of claim 1, wherein the usage information includes a utilization rate, the computer-implemented method further comprising:

calculating a confidence factor based on the utilization rate; and sending the confidence factor to the remote server for use in determining an aggregate rating of the application.

7. A system to rate applications based on weighted emotional states, the system comprising:

one or more computer processors; and a memory containing computer program code that, when executed by operation of the one or more computer processors, performs an operation comprising:

monitoring execution of an application on a computing device to determine usage information for a user;

capturing, via a user-facing camera of the computing device, a plurality of images of the user's face;

for each of the plurality of images:

extracting, from the respective image, a set of user facial features; and determining an user emotional state corresponding to the respective set of user facial features by applying a facial-emotional model correlating a set of predefined emotional states with corresponding predefined facial features;

determining a trend of the user emotional states across a plurality of executions of the application on the computing device;

calculating a rating for the application based on: (i) the usage information; (ii) the trend of user emotional states; and (iii) the user emotional states weighted by at least one of: (A) a demographic factor comprising a specified age group to which the user belongs and (B) an expressiveness factor comprising a variance of emotional expression of the user; and sending, via a network connection, the rating to a server configured to determine an aggregate rating of the application.

8. The system of claim 7, wherein each of the user emotional states is represented by a respective numeric value, and wherein calculating the rating for the application further comprises calculating an average of the respective numeric values.

9. The system of claim 7, wherein capturing the plurality of images is performed over a predefined period of time.

10. The system of claim 7, wherein capturing the plurality of images is performed over a predefined number of executions of the application.

11. The system of claim 7, wherein the sending the rating to the remote server occurs automatically a predefined period of time after the application is downloaded.

12. The system of claim 7, wherein the usage information includes a utilization rate, and the operation further comprising:

calculating a confidence factor based on the utilization rate; and sending the confidence factor to the remote server for use in determining an aggregate rating of the application.

13. A computer-readable storage medium containing computer program code executable to perform an operation to rate applications based on weighted emotional states, the operation comprising:

monitoring execution of an application on a computing device to determine usage information for a user;

capturing, via a user-facing camera of the computing device, a plurality of images;

for each of the plurality of images and by operation of one or more computer processors of the computing device when executing the computer program code:

extracting, from the respective image, a set of user facial features; and determining an user emotional state corresponding to the respective set of user facial features by applying a facial-emotional model correlating a set of predefined emotional states with corresponding predefined facial features;

determining a trend of user emotional states across a plurality of executions of the application on the computing device;

calculating a rating for the application based on: (i) the usage information; (ii) the trend of user emotional states; and (iii) the user emotional states weighted by at least one of: (A) a demographic factor comprising a specified age group to which the user belongs and (B) an expressiveness factor comprising a variance of emotional expression of the user; and sending, via a network connection, the rating to a server configured to determine an aggregate rating of the application.

14. The computer-readable storage medium of claim 13, wherein the user emotional state is determined based further on a user profile, the operation further comprising performing a predefined calibration operation for the facial-emotional model, the predefined calibration operation including:

for each predefined emotional state in the set of predefined emotional states:

requesting the user to intentionally display a facial expression corresponding to the respective predefined emotional state; and capturing one or more images depicting the respective corresponding facial expression;

generating the user profile based upon the captured one or more images; and refining the facial-emotional model, based upon the user profile.

15. The computer-readable storage medium of claim 14, wherein each of the user emotional states is represented by a respective numeric value, wherein calculating the rating for the application further comprises calculating an average of the respective numeric values, wherein the operation further comprises:

determining the specified age group to which the user belongs.

16. The computer-readable storage medium of claim 15, wherein the plurality of images is captured over a predefined period of time and over a predefined number of executions of the application, wherein the operation further comprises, subsequent to determining the user emotional state corresponding to the respective set of user facial features for each of the plurality of images, and prior to calculating the rating for the application:

measuring the variance of emotional expression of the user, based on the plurality of images and the facial-emotional model.

17. The computer-readable storage medium of claim 16, wherein the rating is sent to the remote server automatically upon a predefined period of time elapsing subsequent to downloading of the application.

18. The computer-readable storage medium of claim 17, wherein the user emotional state is determined based further on a user profile, wherein the user profile is based on historical information of the user, wherein the operation further comprises:

sending a confidence factor to the remote server for use in determining the aggregate rating of the application; and     outputting: (i) the rating of the application and (ii) the aggregate rating of the application.

19. The computer-implemented method of claim 1, wherein the user emotional state is determined based further on a user profile.

20. The system of claim 7, wherein the user emotional state is determined based further on a user profile.

\* \* \* \* \*